United States Patent
Siess et al.

(10) Patent No.: US 12,303,680 B2
(45) Date of Patent: May 20, 2025

(54) BLOOD PUMP

(71) Applicant: Abiomed Europe GmbH, Aachen (DE)

(72) Inventors: Thorsten Siess, Aachen (DE); Walid Aboulhosn, Aachen (DE); Frank Kirchhoff, Aachen (DE); Christoph Nix, Aachen (DE); Gerd Bruno Spanier, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 304 days.

(21) Appl. No.: 17/230,035

(22) Filed: Apr. 14, 2021

(65) Prior Publication Data

US 2021/0299433 A1    Sep. 30, 2021

Related U.S. Application Data

(63) Continuation of application No. 16/077,674, filed as application No. PCT/EP2017/053074 on Feb. 10, 2017, now Pat. No. 11,020,584.

(30) Foreign Application Priority Data

Feb. 11, 2016  (EP) .................................... 16155240

(51) Int. Cl.
*A61M 60/857* (2021.01)
*A61M 60/135* (2021.01)
(Continued)

(52) U.S. Cl.
CPC ........ *A61M 60/857* (2021.01); *A61M 60/148* (2021.01); *A61M 60/17* (2021.01);
(Continued)

(58) Field of Classification Search
CPC .... A61M 1/1008; A61M 1/122; A61M 1/125; A61M 2205/0216; A61M 2205/0266; A61M 2205/0272
See application file for complete search history.

(56) References Cited

U.S. PATENT DOCUMENTS

| 6,007,478 A | 12/1999 | Siess et al. |
| 2010/0268017 A1* | 10/2010 | Siess ................... A61M 60/857 600/16 |

(Continued)

FOREIGN PATENT DOCUMENTS

| JP | H06269494 A | 9/1994 |
| JP | 2007501644 A | 2/2007 |

(Continued)

OTHER PUBLICATIONS

International Search Report and Written Opinion from corresponding application No. PCT/EP2017/053074, 8 pages.

(Continued)

*Primary Examiner* — Scott Luan
(74) *Attorney, Agent, or Firm* — Botos Churchill IP Law LLP

(57) ABSTRACT

A blood pump comprises a pump section and a flow cannula. A proximal end portion of the flow cannula is connected to the pump section such that blood can enter the blood flow inlet, and a distal end portion of the flow cannula includes at least one blood flow-through opening for blood to enter the flow cannula. The distal end portion comprises an enlarged diameter portion, with at least a major portion of the blood flow-through opening being disposed in the enlarged diameter portion. The blood pump further comprises a sleeve overlapping the enlarged diameter portion. The sleeve has a structure that prevents its distal end from bending radially inwards into the blood flow-through openings.

22 Claims, 10 Drawing Sheets

(51) Int. Cl.
  *A61M 60/148* (2021.01)
  *A61M 60/17* (2021.01)
  *A61M 60/216* (2021.01)
  *A61M 60/408* (2021.01)

(52) U.S. Cl.
  CPC ........ *A61M 60/216* (2021.01); *A61M 60/408* (2021.01); *A61M 2205/0216* (2013.01); *A61M 2205/0266* (2013.01); *A61M 2205/0272* (2013.01)

(56) References Cited

U.S. PATENT DOCUMENTS

| | | |
|---|---|---|
| 2014/0005467 A1 | 1/2014 | Farnan et al. |
| 2014/0255176 A1* | 9/2014 | Bredenbreuker ..... F04D 29/247 415/208.1 |
| 2023/0099453 A1 | 3/2023 | Siess |

FOREIGN PATENT DOCUMENTS

| | | |
|---|---|---|
| JP | 2010503495 A | 2/2010 |
| WO | 2008034068 A2 | 3/2008 |

OTHER PUBLICATIONS

Office Action issued in corresponding Japanese Patent Application No. 2018-542790 dated Jan. 12, 2021, 7 pages.
Office Action from Korean Patent Application No. 10-2018-7026095 dated Aug. 7, 2023 (17 pp.).
Office Action from corresponding Japanese Patent Application No. 2023-125932 dated May 7, 2024 (8 pp.).

* cited by examiner

BLOOD PUMP

CROSS-REFERENCE TO RELATED APPLICATIONS

This application is a continuation of U.S. patent application Ser. No. 16/077,674, filed Aug. 13, 2018, now U.S. Pat. No. 11,020,584, which is a national phase entry under 35 U.S.C. § 371 of International Application No. PCT/EP2017/053074, filed Feb. 10, 2017, which claims the benefit of European Patent Application No. 16155240.1, filed Feb. 11, 2016, the disclosures of all of which are incorporated herein by reference in their entirety.

BACKGROUND

This invention relates to a blood pump, in particular an intravascular blood pump, to support a blood flow in a patient's blood vessel.

Blood pumps of different types are known, such as axial blood pumps, centrifugal blood pumps or mixed-type blood pumps, where the blood flow is caused by both axial and radial forces. Intravascular blood pumps are inserted into a patient's vessel such as the aorta and into a cardiac valve by means of a catheter. A blood pump typically comprises a pump section with a blood flow inlet and a blood flow outlet. In order to cause a blood flow from the blood flow inlet to the blood flow outlet, typically an impeller or rotor is rotatably supported within the pump casing about an axis of rotation for conveying blood. The blood pump may be driven by a motor included in the blood pump adjacent to the pump section or may alternatively be driven by a motor outside the patient's body, in which case the motor is connected to the impeller by a flexible drive shaft extending through the catheter.

The blood pump may be connected to a flow cannula that is in flow communication with the pump section and that may extend through a cardiac valve, such as the aortic valve, while the pump section or at least the blood flow outlet of the pump section is located in a blood vessel, such as the aorta, outside the patient's heart. The flow cannula has at least one blood flow-through opening for blood to enter the flow cannula towards the blood flow inlet of the pump section. Since the blood flow-through openings of the flow cannula are located within the patient's heart, such as the left ventricle, soft tissue, such as filaments in the left ventricle, may be sucked into the blood flow-through openings. This is to be avoided for several reasons. On the one hand, harm to the soft tissue is to be avoided. On the other hand, if the blood flow-through openings are blocked, this leads to failure of the blood pump and the blood pump has to be removed or at least repositioned.

SUMMARY OF THE INVENTION

It is an object of the present invention to provide a blood pump that provides improved blood flow conditions at the blood flow inlet, in particular at blood flow-through openings of a flow cannula.

This object is achieved according to the present invention by a blood pump having the features of independent claim 1. Preferred embodiments and further developments of the invention are specified in the claims dependent thereon.

According to the invention the blood pump comprises a flow cannula, such as an inflow cannula, a proximal end portion of which is connected to the pump section such that blood can enter the blood flow inlet of the pump section. A distal end portion of the flow cannula comprises an enlarged diameter portion and at least one radial blood flow-through opening for blood to enter the flow cannula. At least a major portion of the blood flow-through opening is disposed in the enlarged diameter portion. The blood pump further comprises a sleeve having a proximal end attached to the flow cannula, in particular the distal end portion thereof, proximal to the blood flow-through opening, and a distal end covering or overlapping the enlarged diameter portion.

The sleeve has a structure that prevents at least the distal end from bending radially inwards by more than 0.2 mm into the at least one blood flow-through opening during unobstructed operation of the blood pump in a patient. Unobstructed operation of the blood pump means the operation mode during unobstructed, normal and typical conditions within a patient's body, e.g., operation of the blood pump with a flow rate of approximately 4 to 5 liters per minute. Preferably, the sleeve has a reinforcement structure that prevents the sleeve from collapsing during operation of the blood pump, as described in more detail below.

The aforementioned features and in particular their combination can improve the blood flow at the blood flow inlet of the pump, in particular at the blood flow-through openings of the flow cannula, which are typically located within a patient's heart during operation of the blood pump. In other words, the blood pump of the present invention provides improved inflow characteristics. In particular, tissue, e.g., filaments in the left ventricle of a patient's heart, can be prevented from being sucked into the blood flow-through openings, which would block the openings. This can already be improved by providing the enlarged diameter portion of the flow cannula, but is significantly improved by providing a sleeve that covers or overlaps the enlarged diameter portion, i.e., in particular part of the blood flow-through openings. Still further improvement of the inflow characteristics can be achieved by providing the sleeve with a structure or reinforcement structure that prevents the sleeve from collapsing and being sucked into the blood flow-through openings itself during operation of the blood pump. In addition, said reinforcement keeps the sleeve conical in shape and therefore allows a gradual increase in blood speed as blood enters the distal end of the cannula. Moreover, the amount of blood drawn into the blood flow-through openings, i.e., the flow rate, can be increased by providing a sleeve that directs the blood flow towards the blood flow-through openings.

According to one aspect, at least the distal end portion of the flow cannula is radially expandable from a compressed or collapsed configuration to an expanded configuration. In particular, the expanded configuration may define the enlarged diameter portion, while in the compressed or collapsed configuration a diameter of the enlarged diameter portion may be substantially equal to a diameter of a remainder of the flow cannula, which may likewise be expandable or may have a fixed diameter. The expanded configuration providing the enlarged diameter portion helps to avoid tissue suction into the flow cannula and enhance blood flow dynamics, while the compressed or collapsed configuration allows the blood pump to be delivered through an introducer sheath. In order to provide expansion properties, the distal end portion of the flow cannula may comprise a shape-memory alloy material, such as Nitinol.

It is noted that enlarging the inflow diameter of the cannula leads to a reduced suction at the inflow cannula and to a reduction in the extent to which tissue sucked into the inflow area affects blood flow into the cannula. In other words, tissue sucked into the smaller diameter of the cannula will have a much greater effect on flow volume into the cannula than if the same amount of tissue is sucked into a larger diameter, assuming equal flow and pressure conditions in the inflow area.

The distal end portion of the flow cannula, in particular the enlarged diameter portion and more particularly the expandable enlarged diameter portion, may comprise a frame structure, such as a cage, that defines the blood flow-through openings. The frame structure may define a plurality of struts that preferably extend axially, i.e., substantially in a direction of the flow cannula's longitudinal axis. It will be appreciated that other designs of struts are possible, such as radial struts, helical struts or struts enclosing an angle with the longitudinal axis, or combinations thereof. The at least one blood flow-through opening may be disposed on a radially circumferential surface of the distal end portion of the flow cannula. Radial openings are preferred to axial openings, as they may reduce tissue suction.

Preferably, the sleeve comprises a membrane of a flexible material, preferably polyurethane or any other suitable biocompatible material, particularly polymer. The membrane may have a thickness of about 0.05 to 0.3 mm, such as 0.1 mm. As for the dimensions of the sleeve in a longitudinal direction, the sleeve may extend along at least a portion of the enlarged diameter portion of the respective blood flow-through opening, e.g., half-way along the enlarged diameter portion. For example, the distal end of the sleeve may be disposed substantially at a largest diameter of the enlarged diameter portion or between the proximal end of the sleeve and the largest diameter of the enlarged diameter portion. Preferably, the sleeve is disposed about a circumferential surface of the distal end portion of the flow cannula. In an alternative embodiment, the sleeve may be disposed within an interior of the flow cannula, in particular the frame structure.

The sleeve may have a funnel shape in order to direct the blood flow into the blood flow-through openings of the flow cannula. That is to say, a diameter of the sleeve increases towards its distal end to provide a tapered shape. In particular, it is advantageous if the sleeve only tapers in one direction, i.e., that its diameter does not decrease after reaching a largest diameter. A funnel shape is particularly useful for increasing the amount of blood that is drawn into the blood flow-through openings, as it gradually increases the linear blood velocity as blood enters the funnel-shaped structure. For example, the flow rate may be increased by 0.5 liters per minute compared to a blood pump without the sleeve.

According to one aspect, the sleeve may be configured to radially expand or unfold and to collapse, preferably as a result of the blood flow. In particular, the sleeve may comprise an expansion mechanism allowing the sleeve to expand or unfold and to collapse. The expansion mechanism may for instance comprise at least one of at least one hinge, at least one magnet, a shape-memory alloy or bimetal. In addition, or alternatively, such expansion mechanism may be included in the flow cannula, in particular its enlarged diameter portion, more particularly in the aforementioned frame structure.

The sleeve may comprise a guiding structure at an inner surface of the sleeve, such as at least one or a plurality of stator blades. The guiding structure may prevent the blood flow from rotating and creating a vortex which would dissipate the blood's potential energy and may direct the blood flow in a longitudinal direction.

According to one aspect, as briefly outlined hereinabove, the blood pump may comprise a reinforcement structure that provides increased stiffness in a radial direction to prevent radial collapse of the sleeve. That is to say, the reinforcement structure ensures that a cross-sectional area of the sleeve at least in a region where the reinforcement structure is disposed is convex, e.g., circular, during operation of the blood pump in a plane perpendicular to the longitudinal axis. Generally, a "convex" cross-sectional area means that the cross-sectional area only has radially outwardly curved or straight edges that do not form any indentations, undercuts or radially inwardly bent portions with respect to a plane perpendicular to the longitudinal axis. Preferably, the reinforcement structure is disposed at least in or adjacent to the distal end of the sleeve. In other words, it is advantageous or may even be sufficient if the open end of the sleeve, i.e., the end at which blood enters the sleeve, is reinforced so that it does not collapse but is maintained open to allow blood to enter the sleeve and the blood flow-through openings of the flow cannula during operation of the blood pump. It will be appreciated, however, that the reinforcement structure nevertheless may be collapsible, in particular for insertion or removal of the blood pump through a catheter, as described in more detail below. That is to say, during operation of the blood pump, the reinforcement can withstand any forces that occur, in particular radial forces, such that the sleeve does not collapse. However, if a sufficiently high force is applied, e.g., during removal or during preparation of the blood pump before insertion into a catheter, the radial stiffness of the reinforcement structure may be overcome to collapse or fold the sleeve into a collapsed configuration.

Therefore, according to one aspect, the reinforcement structure may be radially expandable or unfoldable from a collapsed configuration to an expanded configuration, which allows the blood pump to be delivered through an introducer sheath. Preferably, the reinforcement structure is conversely also collapsible or foldable to facilitate removal of the blood pump from a patient's body. Again, at the same time, the reinforcement structure may provide sufficient stiffness in the expanded configuration to prevent the sleeve from collapsing during operation of the blood pump. However, the reinforcement structure may be designed such that it can be collapsed by applying a sufficiently high force, e.g., by drawing the blood pump into a catheter for removal from the patient's body.

In one embodiment, the structure of the sleeve or particularly the reinforcement structure may comprise at least one inflatable structure that extends at least partially circumferentially about the sleeve. The reinforcement structure may for instance comprise at least one annular balloon. The balloon may be disposed on an outer surface of the sleeve such that it protrudes radially outwards from the sleeve and helps to keep soft tissue away from the blood flow-through openings. Alternatively, or in addition to an annular balloon, the entire sleeve may be inflatable or may comprise a not only annular structure that reinforces the sleeve and prevents the sleeve from collapsing. Further inflatable structures may be provided with the flow cannula to increase stiffness or to keep soft tissue away from the inlet openings. For example, a soft tip, such as a pigtail or J-tip, which may be inflatable, may be provided at the cannula's distal end. It will be appreciated that any of the aforementioned inflatable structures may also be deflatable to facilitate removal from a patient's body.

Alternatively, or in addition, the structure of the sleeve or particularly the reinforcement structure may comprise at least one resilient member that extends at least partially circumferentially about the sleeve. For example, the reinforcement structure may comprise at least one band or wire extending at least partially circumferentially about the sleeve and comprising at least one of a shape-memory alloy, a metal and polymer material. The band or wire may extend along the circumference of the sleeve either along a straight line or with undulations or a zig-zag shape.

Alternatively, or in addition, the structure of the sleeve or particularly the reinforcement structure may comprise at least one telescoping member that extends at least partially circumferentially about the sleeve. The telescoping member may for instance comprise a tube portion and a wire portion attached to an end of the tube portion such that a free end of the wire portion can be inserted into a free end of the tube portion to form a telescoping ring. The telescoping member may be made from a shape-memory alloy, such as Nitinol.

In one embodiment, at least two sleeves, such as two, three or four sleeves, may be disposed in series on the distal end portion of the flow cannula such that blood can enter each of the sleeves towards the blood flow-through openings. For example, the sleeves may be arranged such that the proximal end of one sleeve is disposed in a region of the distal end of an adjacent sleeve and blood can enter the distal end of each sleeve. Alternatively, the distal end of one sleeve may be connected with the proximal end of an adjacent sleeve by means of a structure that provides openings such that blood can enter each of the sleeves from the distal end. The sleeves may be arranged in the manner of pine-cone scales or may form a caterpillar-like shape.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
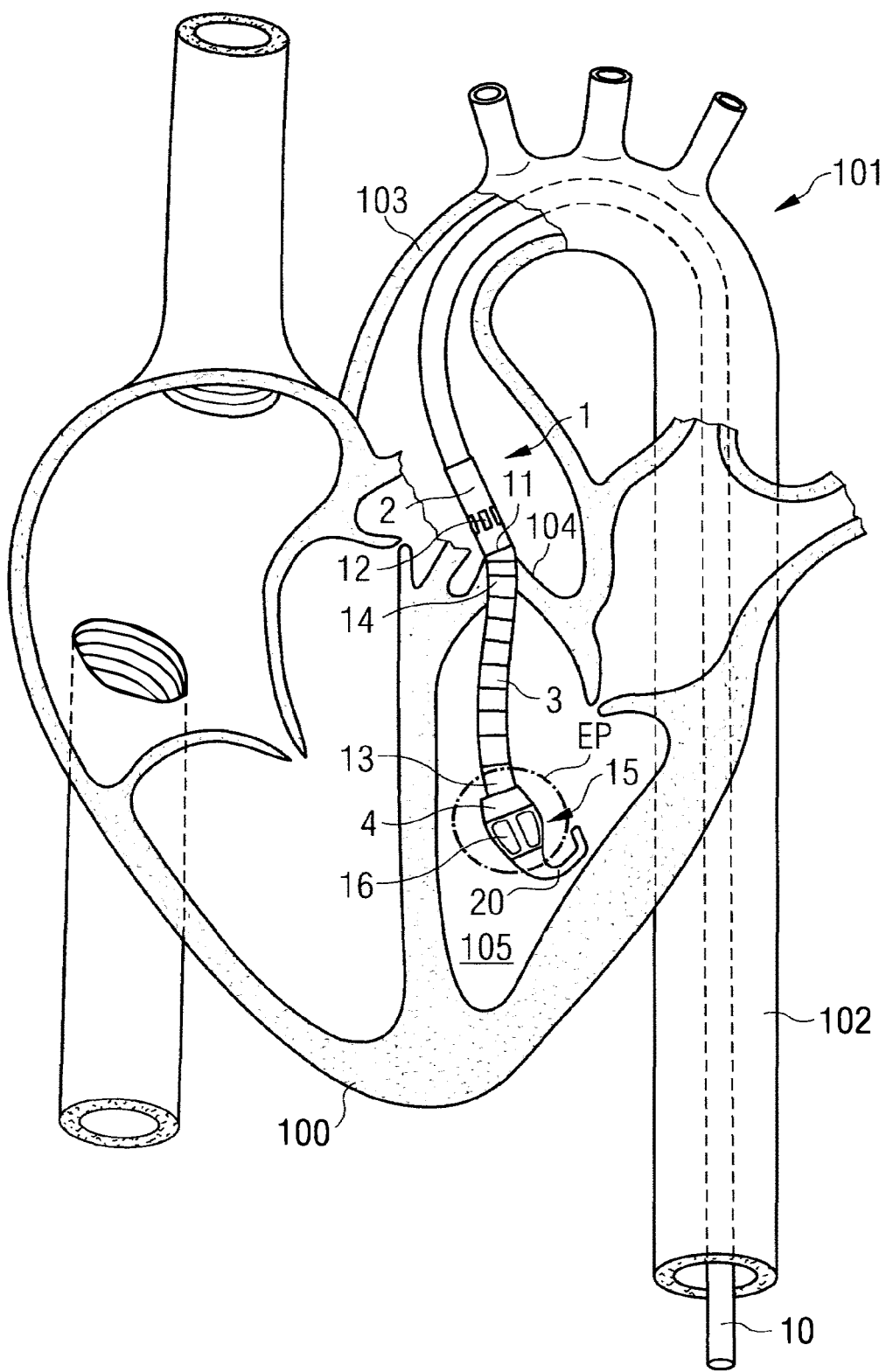
FIG. 1 shows a partial cross-sectional view of a patient's heart with one embodiment of a blood pump.

In FIG. 1 a blood pump 1 is illustrated inserted into a patient's heart 100. More specifically, the blood pump 1 is connected to a catheter 10 by means of which the blood pump 1 is inserted into the left ventricle 105 of the patient's heart 100 via the aorta 101, including the descending aorta 102 and the aortic arch 103. During operation, the blood pump 1 is placed through the aortic valve 104. The blood pump 1 comprises a pump section 2 and a flow cannula 3. The pump section 2 has a blood flow outlet 12 that is disposed outside the patient's heart 100 in the aorta 102, while a blood flow inlet of the pump section 2 (indicated at 11) is in flow communication with the flow cannula 3. An impeller (not shown) is provided to cause the blood flow. The flow cannula 3 extends through the aortic valve 104 into the left ventricle 105 and has a proximal end portion 14 connected to the pump section 2 and a distal end portion 13. In order to pump blood through the flow cannula 3 into the pump section 2 and out of the blood flow outlet 12, the distal end section 13 has an enlarged diameter portion 15 with blood flow-through openings 16 that will be described in more detail below. At the distal end of the blood pump 1, a soft tip 20, such as a pigtail or J-tip, is arranged to facilitate insertion of the blood pump 1 into the patient's heart 100 without causing any harm to the surrounding tissue. Also, the soft tip 20 helps to keep soft tissue away from the flow cannula 3. The end portion of the blood pump 1 is indicated at EP, which is shown in more detail in FIG. 2A. Generally, the term "proximal" refers to directions towards a user, while the term "distal" refers to directions away from the user.

Figure 2A:
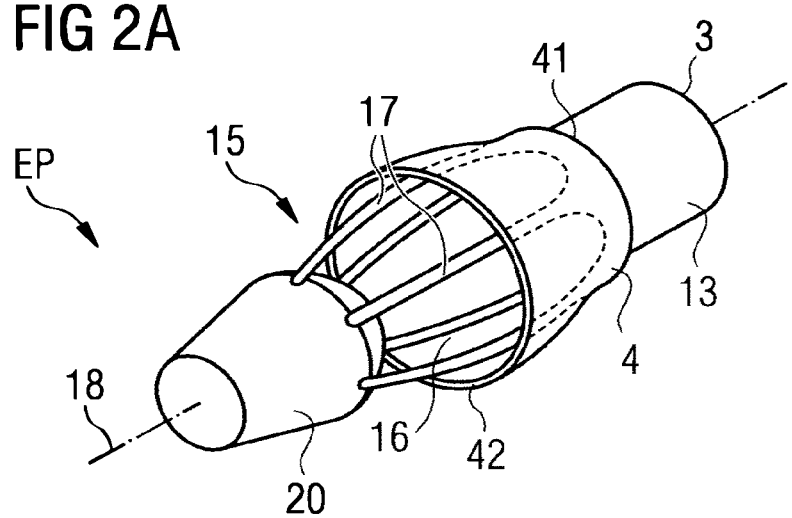
FIGS. 2A to 2C show different views of the end portion of the blood pump of FIG. 1 in a first configuration.
Figure 2B:
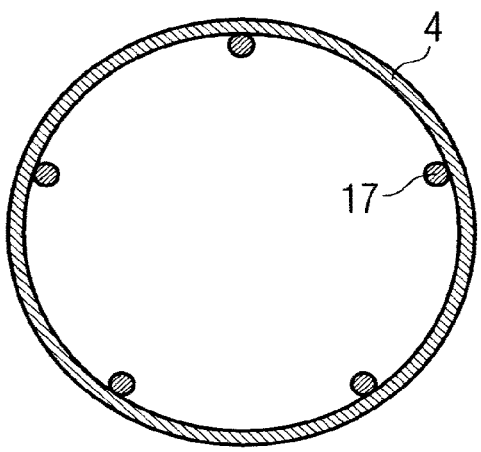
Figure 2C:
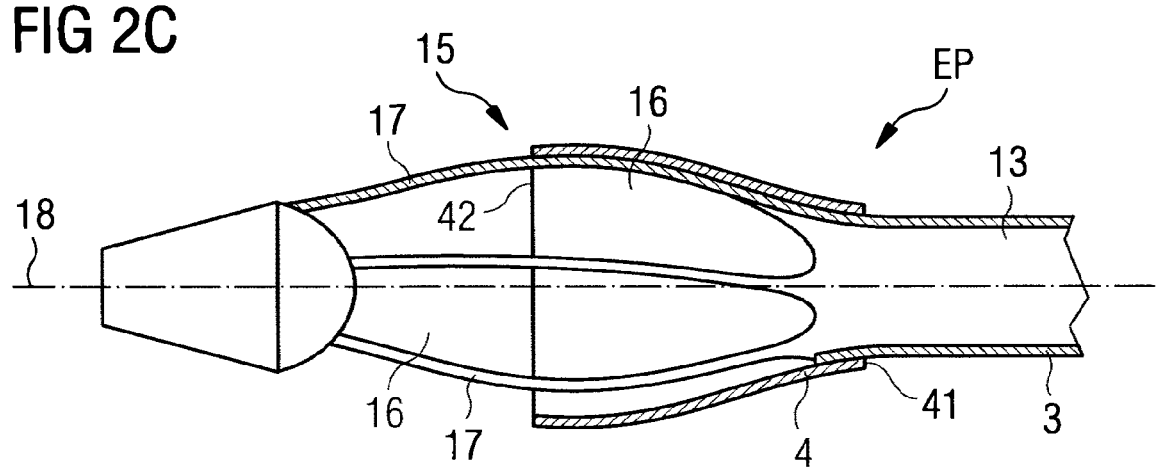

Referring to FIGS. 2A to 2C, the distal end portion EP is shown in more detail in a first configuration during operation of the blood pump 1, i.e., under normal conditions, including heart pressure and flow rate, e.g., a flow rate of 4 liters per minute. The blood flow-through openings 16 are formed by a frame structure, such as a cage that includes struts 17 separating the blood flow-through openings 16 from each other. In this embodiment, the struts 17 are shown extending substantially axially along the longitudinal axis 18 of the flow cannula 3. It will be appreciated that the struts 17 may also extend radially or helically or may form any other suitable shape to form the blood flow-through openings 16. In the present embodiment, five struts 17 form the cage with the blood flow-through openings 16. However, there may be fewer struts, such as three or four, or more struts, such as six, seven or eight.

A sleeve 4 is provided that covers or overlaps a portion of the enlarged diameter portion 15 of the distal end portion 13 of the flow cannula 3, more specifically of the blood flow-through openings 16. The sleeve 4 has a proximal end 41 that is attached to the distal end portion 13 of the flow cannula 3 at a location proximal of the blood flow-through openings 16, and a distal end 42. That is to say, the sleeve 4 covers a proximal portion of the blood flow-through openings 16, for instance the proximal half of the blood flow-through openings 16. By providing the sleeve 4, tissue suction into the blood flow-through openings 16 can be reduced. The sleeve 4 has a funnel shape, i.e., its diameter increases in a direction from the proximal end 41 to the distal end 42. Preferably, the sleeve 4 does not get narrower at its distal end 42. The funnel shape can increase the blood flow rate of the blood pump 1.

As can be seen in FIGS. 2A and 2B, the cross-sectional area of the sleeve 4 in a plane perpendicular to the longitudinal axis 18 is substantially circular. As shown, the sleeve 4 may be supported by the cage. However, the sleeve 4 may provide a larger diameter than the cage. Under certain, ideal conditions the sleeve 4 may be held open by the blood flow and may provide sufficient stability to withstand collapsing during operation of the blood pump 1. This may be achieved by choosing an appropriate material of the sleeve 4 or by providing a reinforcement structure as described in more detail below.

Figure 3A:
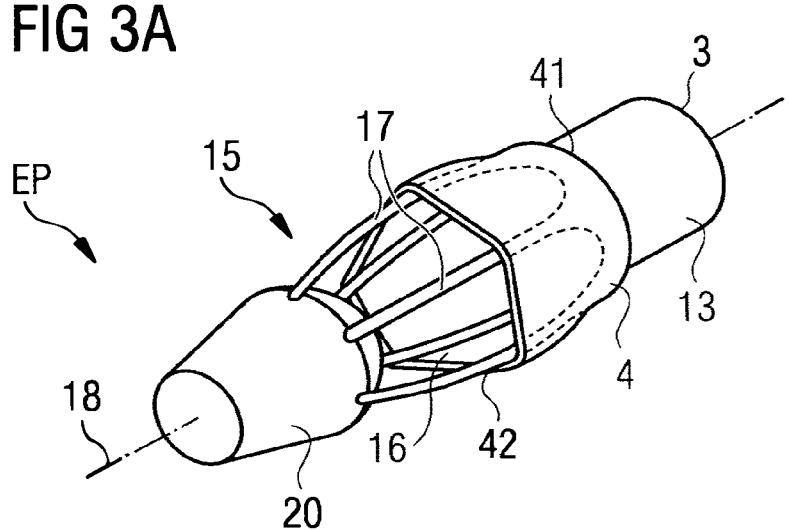
FIGS. 3A and 3B show different views of the end portion of the blood pump of FIG. 1 in a second configuration.
Figure 3B:
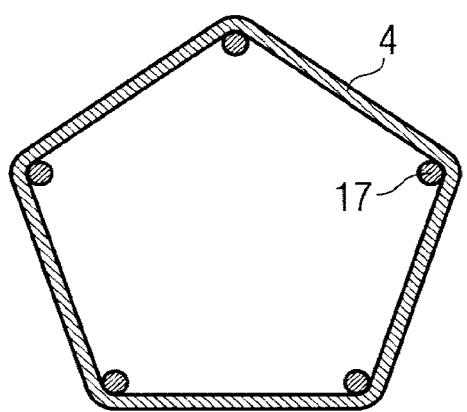
Figure 4A:
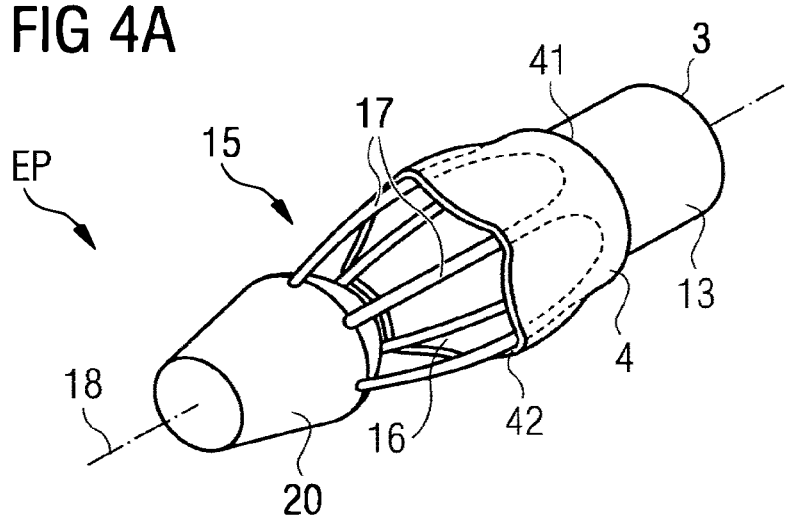
FIGS. 4A and 4B show different views of the end portion of the blood pump of FIG. 1 in a third configuration.
Figure 4B:
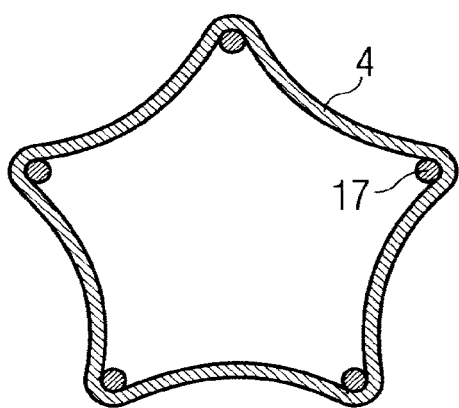

During operation of the blood pump 1, the sleeve 4 may assume other configurations than substantially circular. The sleeve 4 may be tightly fitted around the struts 17 such that a cross-sectional area of the sleeve forms a pentagon if the cage includes five struts 17 as shown in FIGS. 3A and 3B. In particular as a result of the pressure distribution at the distal end 42 of the sleeve 4, the sleeve 4 may also slightly bend inwards from the struts 17 into the blood flow-through openings 16, as shown in FIGS. 4A and 4B. It will be appreciated that the bending should be no more than 0.2 mm at each side radially inwards to avoid adverse effects on the blood flow. In particular, the sleeve 4 has sufficient stiffness to prevent it from being sucked into the blood flow-through openings 16, which could possibly block them.

Generally, the cage as well as the sleeve 4 and possibly also the flow cannula 3 may provide expansion properties. That is to say, the aforementioned parts of the blood pump 1 may assume an expanded configuration providing an enlarged diameter, and a collapsed or compressed configuration providing a smaller diameter. In particular, the enlarged diameter portion 15 may be defined in the expanded configuration, while in the compressed configuration the diameter of the portion 15 may be substantially the same as the diameter of the remainder of the flow cannula 3 to allow the blood pump 1 to be delivered through an introducer sheath. When delivered at the target site, e.g., the patient's heart as described above in connection with FIG. 1, the blood pump 1 may be released to assume the expanded configuration.

Although the sleeve 4 may have a structure that provides sufficient radial stiffness to prevent the sleeve 4 from collapsing during operation of the blood pump 1, e.g., a structure comprising a membrane of an appropriate material, such as polyurethane, an additional reinforcement structure may be provided that is attached to or embedded in the sleeve 4. It will be appreciated that the reinforcement structure provides radial stiffness during operation of the blood pump 1, but at the same time provides expansion and compression characteristics as described above to allow the blood pump to assume an expanded or unfolded configuration and a compressed or collapsed configuration.

Figure 5A:
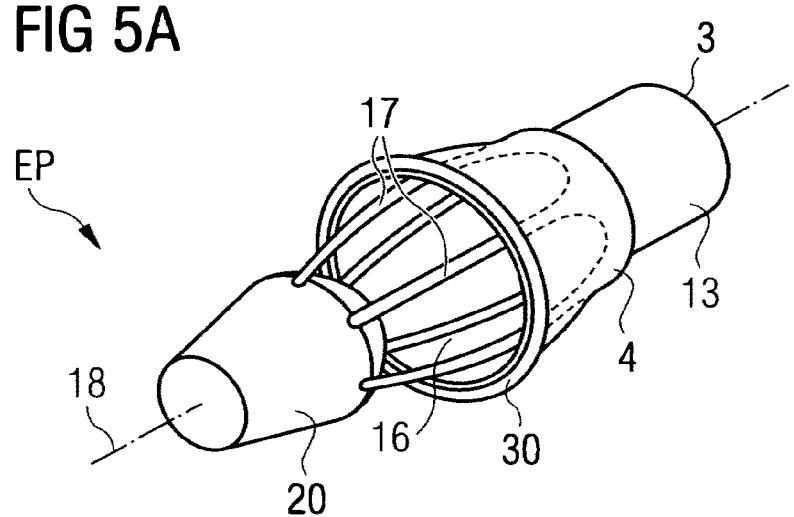
FIGS. 5A and 5B show different views of the end portion of a blood pump according to another embodiment.
Figure 5B:
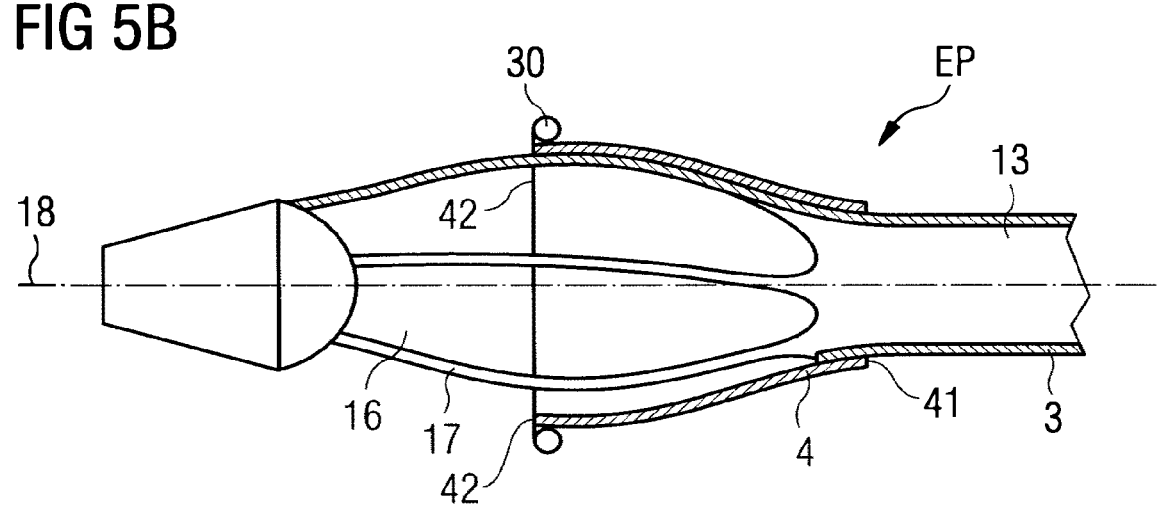

Referring to FIGS. 5A and 5B, the sleeve 4 has a reinforcement structure in the form of an inflatable device such as an annular balloon 30. The balloon 30 may be inflated and also deflated via a pipe (not shown) with a suitable fluid, such as a gas or liquid. The balloon 30 may be attached to an outer circumference of the distal end 42 of the sleeve 4 or may be attached to the balloon 30 at any other suitable location or may be embedded in the sleeve 4. Moreover, more than one inflatable annular balloon may be provided or another inflatable structure that provides radial stiffness for the sleeve 4. Preferably, the inflatable structure is also deflatable to facilitate removal of the blood pump 1 from the patient's body.

Figure 6:
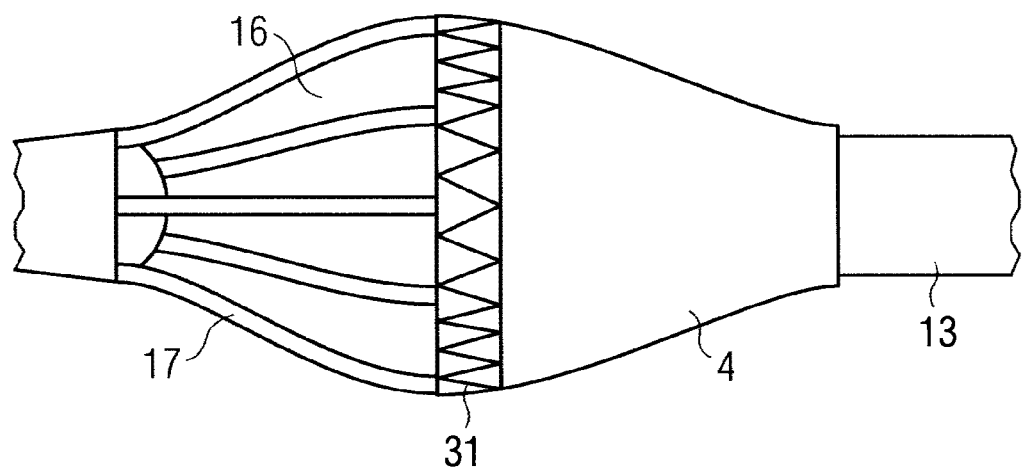
FIG. 6 shows a side elevation view of the end portion of a blood pump according to another embodiment.
Figure 7:
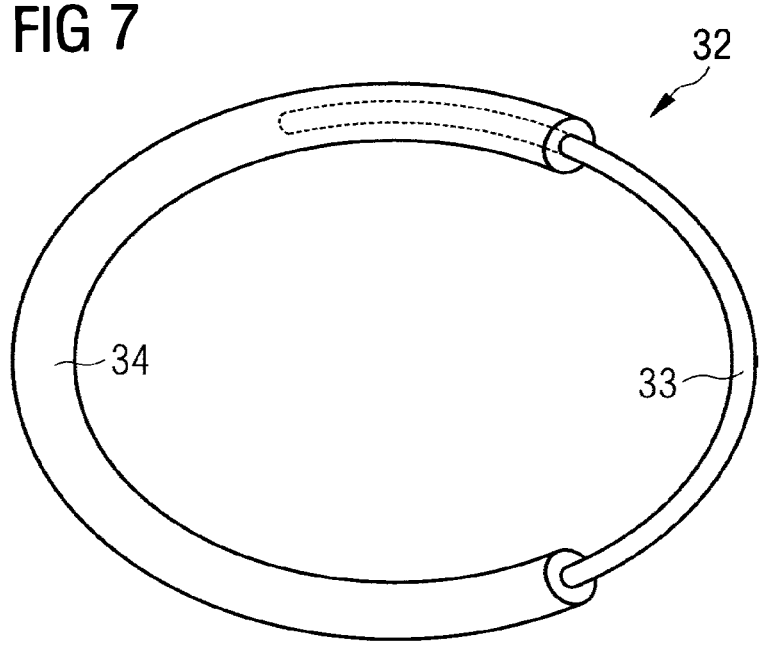
FIG. 7 shows a reinforcement member for a sleeve.

Further embodiments of a reinforcement structure that may be used alternatively to the inflatable balloon 30 or possibly in addition thereto are shown in FIGS. 6 and 7. In FIG. 6 is illustrated a reinforcement structure formed by a band 31 comprising a shape-memory alloy, such as Nitinol. For example, the band 31 may comprise a zig-zag structure of a Nitinol wire. However, the band 31 may comprise other structures that provide radial stiffness during operation of the blood pump 1 and at the same time expansion and compression properties, or may comprise other materials such as metal or polymer.

The reinforcement structure shown in FIG. 7 is formed by a telescoping member 32. The telescoping member 32 comprises a tube portion 34 and a wire portion 33 attached to the tube portion 34 with a free end of the wire portion 33 being slidably insertable into the tube portion 34 to form a telescoping ring. The telescoping member 32 provides radial stiffness for the sleeve 4 but allows variation of its diameter to allow for an expanded and compressed configuration as described above. The band 31 and the telescoping member 32 may be attached to the sleeve 4 at the sleeve's distal end 42 to keep the distal end 42 open. It will be appreciated, however, that the band 31 and the telescoping member 32 may be attached to or embedded in the sleeve 4 at other suitable locations for providing the aforementioned characteristics.

Figure 8:
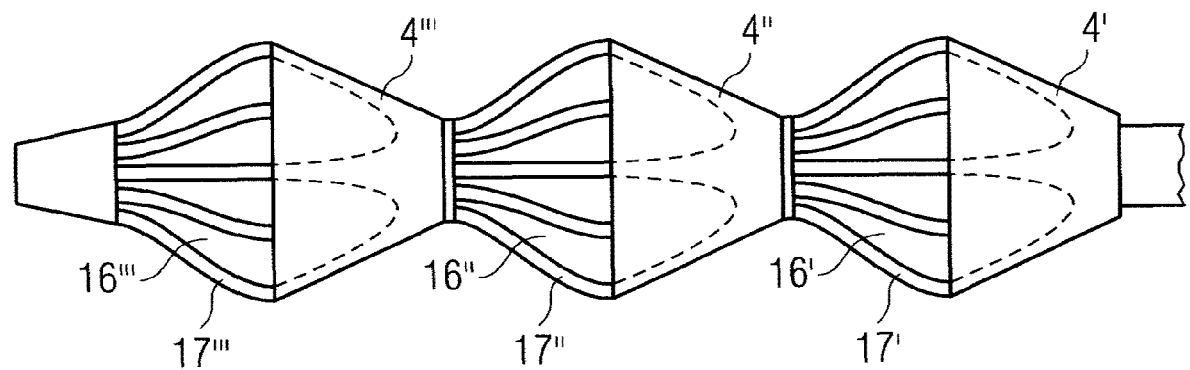
FIG. 8 shows a side elevation view of the end portion of a blood pump according to another embodiment, including more than one sleeve.

FIG. 8 illustrates an embodiment in which more than one, here three, sleeves 4', 4", 4'" overlap respective blood flow-through openings 16', 16", 16'" formed by struts 17', 17", 17'". The blood flow-through openings 16', 16", 16'" and struts 17', 17", 17'" may be formed like the blood flow-through openings 16 and struts 17, respectively, described hereinabove. Likewise, the sleeves 4', 4", 4'" may be formed like the sleeve 4 described hereinabove with or without an additional reinforcement structure. This arrangement may help to keep soft tissue away from the blood flow-through openings.

Figure 9:
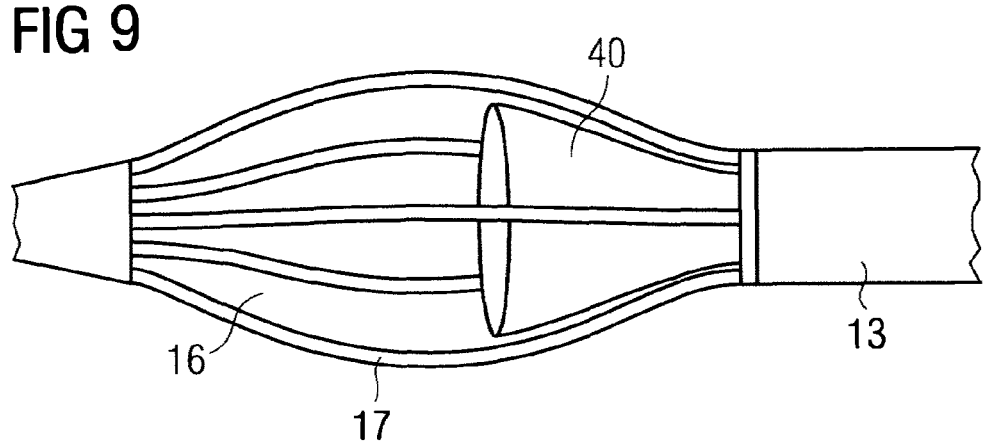
FIG. 9 shows a side elevation view of the end portion of a blood pump according to another embodiment.

Another embodiment of a distal end portion EP of a blood pump is shown in FIG. 9. In this embodiment, the sleeve 40 is disposed within the cage rather than surrounding it. That is to say, the sleeve 40 overlaps the blood flow-through openings 16 from the inside. Blood can enter the sleeve 40 and, thus, the flow cannula 3 without sucking soft tissue. Soft tissue is kept away from the open end of the sleeve by the struts 17. In addition, the sleeve 40 could be attached to the inner surface of the struts 17 (not shown) by means of adhesives or any other means to keep the sleeve 40 open at all times or it could be left free from the struts 17 as shown in FIG. 9. A reinforcing inflatable circular balloon (not shown in FIG. 9) similar to balloon 30 shown in FIGS. 5A and 5B could be used as described above to keep the sleeve 40 open and circular in shape during device use. A telescoping member (not shown in FIG. 9) similar to the telescoping member 32 shown in FIG. 7 could be used as described above to keep sleeve 40 open and circular in shape during device use.

Figure 10A:
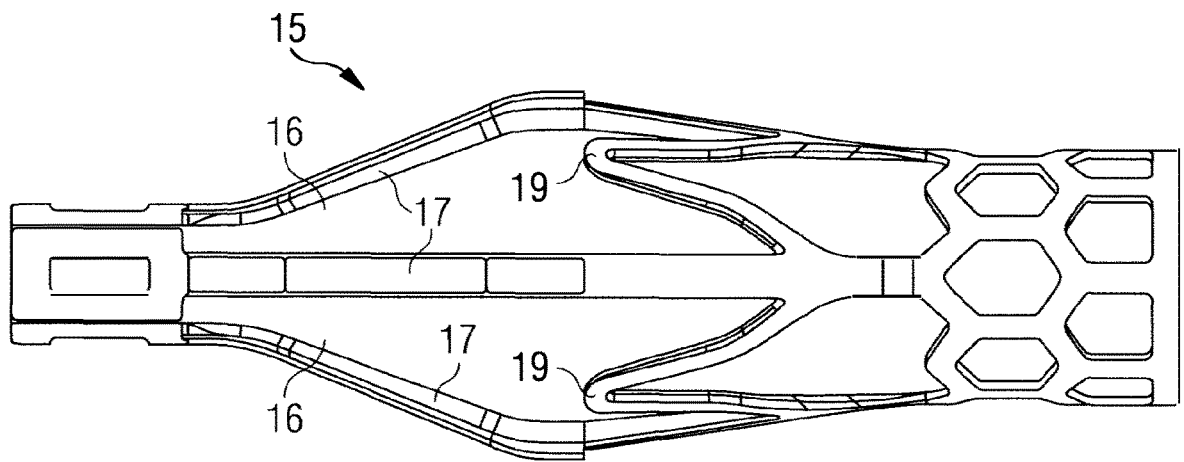
FIGS. 10A and 10B show an inflow cage of an end portion of a blood pump according to another embodiment.
Figure 10B:
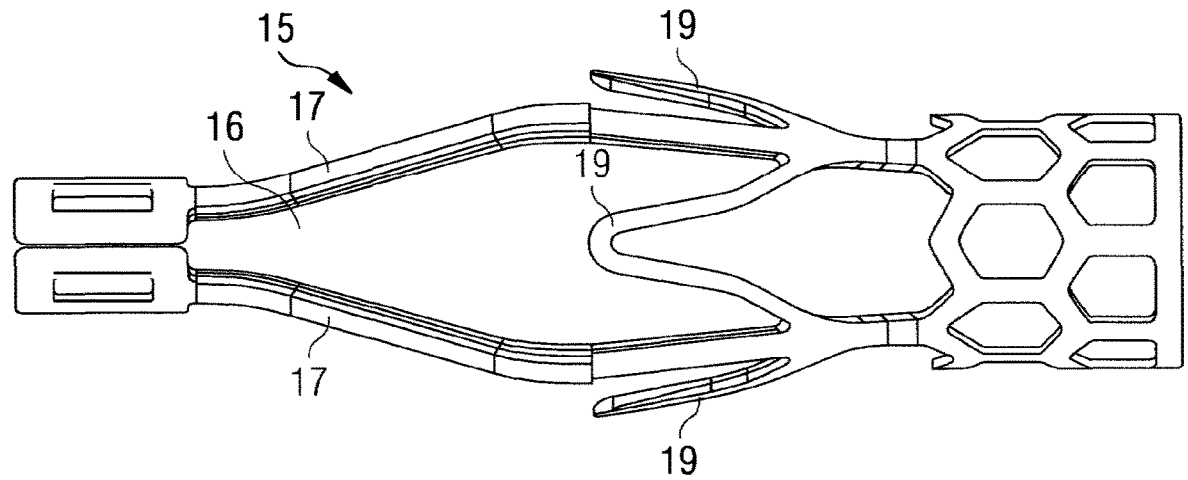

FIGS. 10A and 10B show an inflow cage of an end portion of a blood pump according to another embodiment. This embodiment is substantially similar to the previously described embodiments, wherein like reference numerals refer to like elements. For illustrative purposes the sleeve is omitted in FIGS. 10A and 10B. The inflow cage, which forms the enlarged diameter portion 15, comprises four struts 17 and blood flow through openings 16. The inflow cage further comprises a support structure for providing additional support for the sleeve. The support structure may extend from the proximal end of the inflow cage substantially half the length of the inflow cage or less than half of the inflow cage, or may correspond to the length of the sleeve.

The support structure comprises arches 19 that connect adjacent struts 17, i.e., in this embodiment four arches 19. The arches 19 may have any suitable shape, such as pointed, rounded or otherwise curved and may have a prong-like shape. The arches 19 may be disposed radially inwards relative to the struts 17 or at substantially the same radius as the struts 17 as shown in FIG. 10A or may extend radially outwards beyond the struts 17 as shown in FIG. 10B. In an embodiment, the configuration shown in FIG. 10A may be referred to as a compressed configuration and the configuration shown in FIG. 10B may be referred to as expanded configuration. The inflow cage may be made of a shape memory allow such as Nitinol.

Figure 11A:
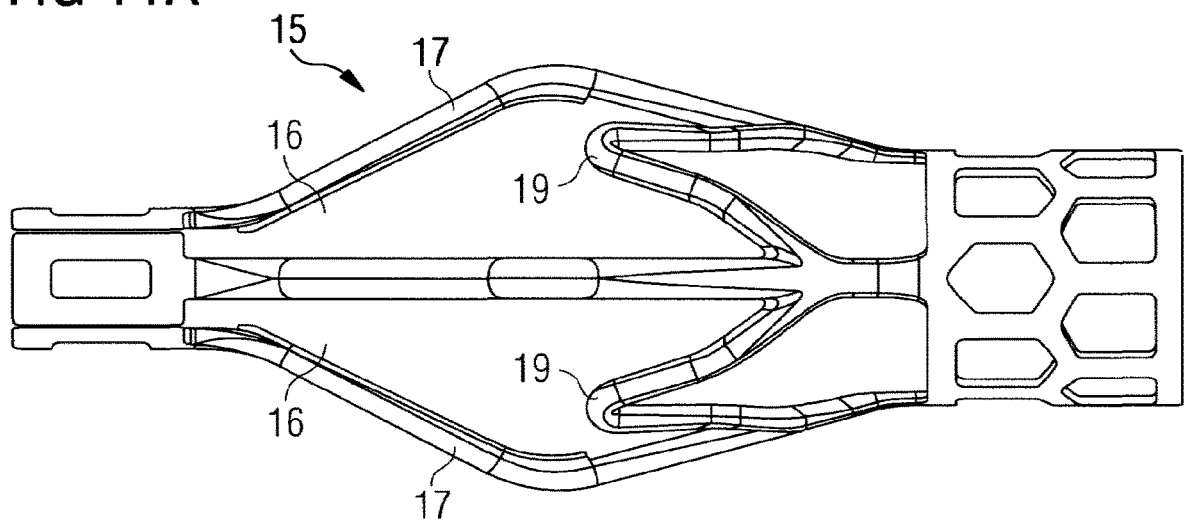
FIGS. 11A and 11B show an inflow cage of an end portion of a blood pump according to another embodiment.
Figure 11B:
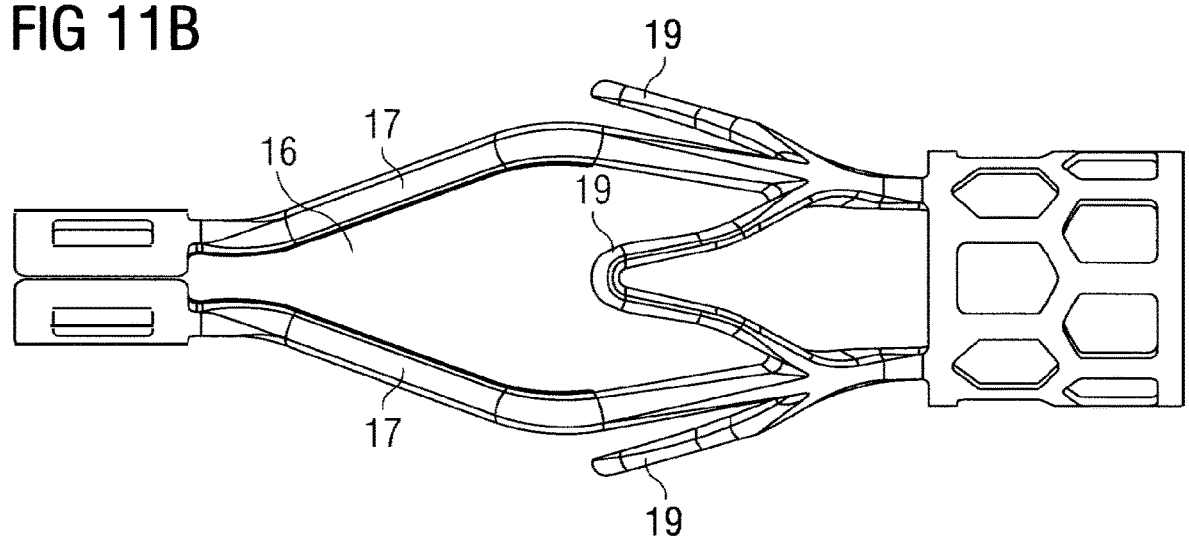

FIGS. 11A and 11B show an inflow cage of an end portion of a blood pump according to another embodiment, which is substantially identical to the embodiment shown in FIGS. 10A and 10B. The inflow cage may be made of Nitinol and may provide different configurations, such as compressed and expanded. As illustrated in FIG. 11A, the arches 19 are disposed radially inwards relative to the struts 17, whereas in FIG. 11B the struts are disposed radially outwards relative to the struts 17.

Figure 12A:
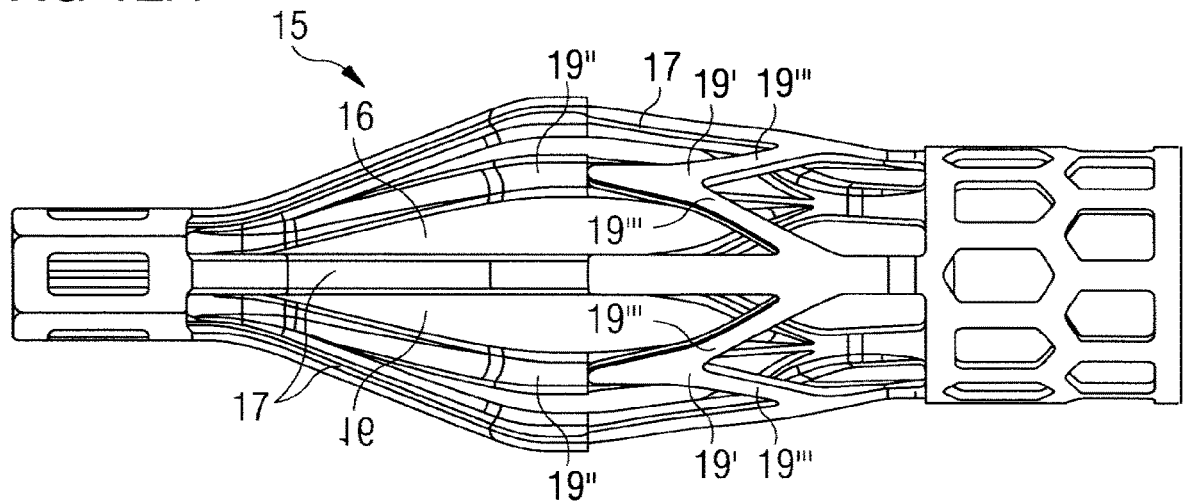
FIGS. 12A and 12B show different views of an inflow cage of an end portion of a blood pump according to another embodiment.
Figure 12B:
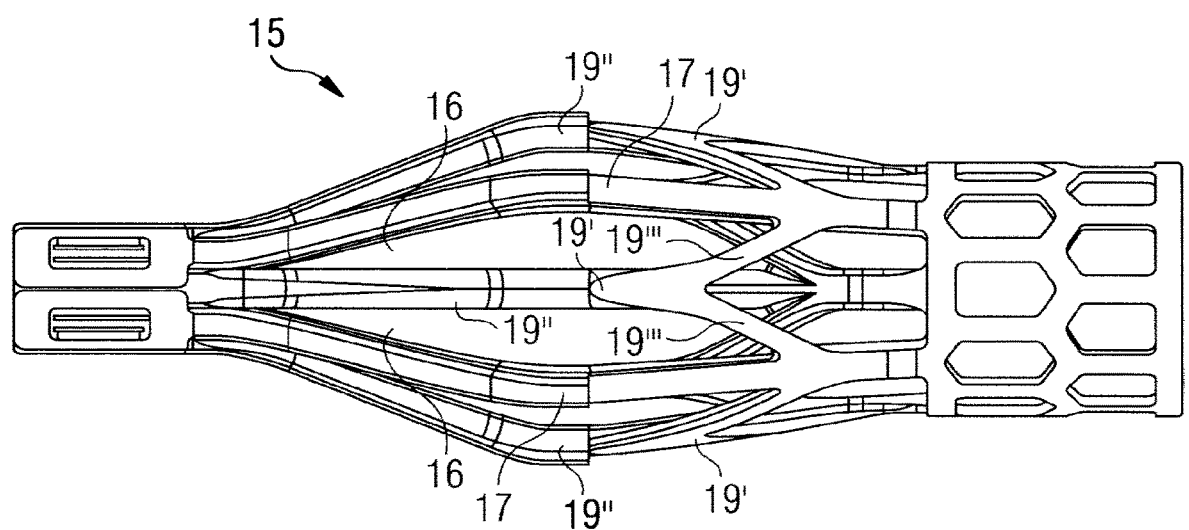

FIGS. 12A and 12B show different views of an inflow cage of an end portion of a blood pump according to another embodiment, which is similar to the embodiment shown in FIGS. 10A and 10B. The inflow cage comprises five struts 17 that are substantially identical to the struts in the other embodiments. The inflow cage comprises a support structure for providing additional support for the sleeve (sleeve not shown in FIGS. 11A and 11B). The support structure comprises additional struts 19" that have a fork 19' towards the proximal end such that the additional struts 19" fork into separate branches 19'''. With reference to the embodiments of FIGS. 10A to 11B, the forks 19' could be regarded as the arches 19, whereby an additional strut 19" is connected to the free distal end of each of the arches 19. Or in other words, the inflow cage of the embodiment of FIGS. 12A and 12B could be regarded as having a plurality of struts 17 and 19" whereby at least some of the struts fork or branch towards their proximal end to form a support structure for a sleeve. The branches 19''' of the respective struts 19" may connect to the adjacent struts 17 as shown in FIGS. 12A and 12B. As in the previous embodiments, the inflow cage is preferably made of Nitinol.

It will be appreciated that the described embodiments are only illustrative but not limiting. In particular, various aspects and features of the embodiments could be combined or independently employed in a different embodiment. For instance, the features described with respect to the sleeve and reinforcement structure could be variably combined without departing from the scope of the invention.

The invention claimed is:

1. A blood pump comprising:
a pump section comprising a blood flow inlet, a blood flow outlet, and an impeller for conveying blood from the blood flow inlet to the blood flow outlet;
a flow cannula comprising a distal end portion and a proximal end portion, wherein the proximal end portion of the flow cannula is connected to the pump section and the distal end portion of the flow cannula comprises an enlarged diameter portion comprising at least one radial blood flow-through opening, formed by one or more struts, for blood to enter the flow cannula, wherein the enlarged diameter portion further includes one or more arches that connect adjacent struts of the one or more struts, wherein the one or more arches form a support structure of the enlarged diameter portion, wherein the support structure extends a distance less than the length of the enlarged diameter portion; and
a sleeve comprising a proximal end attached to the flow cannula and a distal end overlapping at least a portion of the enlarged diameter portion,
wherein the sleeve is configured to radially expand from a compressed configuration to an expanded configuration.

2. The blood pump of claim 1, wherein the sleeve is configured to radially expand as a result of blood entering the flow cannula.

3. The blood pump of claim 1, wherein the sleeve is also configured to radially compress from the expanded configuration to the compressed configuration.

4. The blood pump of claim 3, wherein the sleeve comprises an expansion mechanism allowing the sleeve to expand and to compress.

5. The blood pump of claim 4, wherein the expansion mechanism comprises at least one of a hinge, a magnet, a shape-memory alloy or a bimetal.

6. The blood pump of claim 1, wherein the sleeve comprises a membrane of a flexible material.

7. The blood pump of claim 6, wherein the flexible material comprises polyurethane.

8. The blood pump of claim 1, wherein the sleeve further comprises a reinforcement structure.

9. The blood pump of claim 8, wherein the reinforcement structure is disposed at least in or adjacent to the distal end of the sleeve.

10. The blood pump of claim 8, wherein the reinforcement structure is configured to radially expand from the compressed configuration to the expanded configuration.

11. The blood pump of claim 8, wherein the reinforcement structure comprises at least one inflatable structure.

12. The blood pump of claim 11, wherein the at least one inflatable structure is an inflatable annular balloon.

13. The blood pump of claim 8, wherein the reinforcement structure comprises a band or a wire extending at least partially circumferentially about the sleeve.

14. The blood pump of claim 13, wherein the band or the wire comprises at least one of a shape-memory alloy, a metal or a polymer material.

15. The blood pump of claim 8, wherein the reinforcement structure comprises at least one telescoping member that extends at least partially circumferentially about the sleeve.

16. The blood pump of claim 1, wherein the distal end portion of the flow cannula is connected to a soft tip.

17. The blood pump of claim 16, wherein the soft tip is inflatable.

18. The blood pump of claim 16, wherein the soft tip is a pigtail or a J-tip.

19. The blood pump of claim 1, wherein the blood pump is an intravascular blood pump, an axial blood pump, a centrifugal blood pump, or a mixed-type blood pump.

20. The blood pump of claim 1, wherein the distal end of the sleeve overlaps at least a portion of the enlarged diameter portion on inside of the enlarged diameter portion.

21. The blood pump of claim 1, wherein the distance corresponds to the length of the sleeve overlapping at least the portion of the enlarged diameter portion.

22. A blood pump comprising:
a pump section comprising a blood flow inlet, a blood flow outlet, and an impeller for conveying blood from the blood flow inlet to the blood flow outlet;
a flow cannula comprising a distal end portion and a proximal end portion, wherein the proximal end portion of the flow cannula is connected to the pump section and the distal end portion of the flow cannula comprises an enlarged diameter portion comprising at least one radial blood flow-through opening, formed by one or more struts, for blood to enter the flow cannula, wherein the enlarged diameter portion further includes one or more arches that connect adjacent struts of the one or more struts, wherein the one or more arches form a support structure of the enlarged diameter portion, wherein the support structure extends a distance less than the length of the enlarged diameter portion; and a sleeve comprising a proximal end attached to the flow cannula and a distal end overlapping at least a portion of the enlarged diameter portion, wherein at least the distal end portion of the flow cannula is configured to radially expand from a compressed configuration to an expanded configuration.

* * * * *